United States Patent
Broehl et al.

(10) Patent No.: US 7,810,693 B2
(45) Date of Patent: Oct. 12, 2010

(54) SURGICAL STAPLING AND CUTTING INSTRUMENT WITH ARTICULATABLE END EFFECTOR

(75) Inventors: Joshua Michael Broehl, Worthington, OH (US); Jamison Joseph Float, Westerville, OH (US); James Huang Lua, Columbus, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 280 days.

(21) Appl. No.: 11/807,666

(22) Filed: May 30, 2007

(65) Prior Publication Data
US 2008/0300579 A1    Dec. 4, 2008

(51) Int. Cl.
*A61B 17/00* (2006.01)
(52) U.S. Cl. .................. 227/179.1; 227/19; 227/175.1; 227/178.1
(58) Field of Classification Search ............... 227/175.1, 227/19, 178.1, 179.1
See application file for complete search history.

(56) References Cited

U.S. PATENT DOCUMENTS

| | | |
|---|---|---|
| 2,853,074 A | 9/1958 | Olson |
| 2,959,974 A | 11/1960 | Emrick |
| 3,490,675 A | 1/1970 | Green et al. |
| 3,551,987 A | 1/1971 | Wilkinson |
| 3,643,851 A | 2/1972 | Green et al. |
| 3,662,939 A | 5/1972 | Bryan |
| 3,717,294 A | 2/1973 | Green |
| 3,819,100 A | 6/1974 | Noiles et al. |
| 4,331,277 A | 5/1982 | Green |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,429,695 A | 2/1984 | Green |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,522,327 A | 6/1985 | Korthoff et al. |
| 4,530,453 A | 7/1985 | Green |
| 4,565,109 A | 1/1986 | Tsay |
| 4,566,620 A | 1/1986 | Green et al. |

(Continued)

FOREIGN PATENT DOCUMENTS

CA    2458946 A1    3/2003

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner*—Brian D Nash
(74) *Attorney, Agent, or Firm*—Dean Garner

(57) ABSTRACT

A surgical instrument that has an articulatable end effector. Various types of passive articulation joints are disclosed for interconnecting a proximal frame portion to the end effector to facilitate pivotal travel of the end effector relative to the proximal frame portion of the instrument.

4 Claims, 10 Drawing Sheets

U.S. PATENT DOCUMENTS

| | | |
|---|---|---|
| 4,573,622 A | 3/1986 | Green et al. |
| 4,580,712 A | 4/1986 | Green |
| 4,610,383 A | 9/1986 | Rothfuss et al. |
| 4,629,107 A | 12/1986 | Fedotov et al. |
| 4,655,222 A | 4/1987 | Florez et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,821,939 A | 4/1989 | Green |
| 4,869,414 A | 9/1989 | Green et al. |
| 4,869,415 A | 9/1989 | Fox |
| 4,880,015 A | 11/1989 | Nierman |
| 4,941,623 A | 7/1990 | Pruitt |
| 4,944,443 A | 7/1990 | Oddsen et al. |
| 4,973,274 A | 11/1990 | Hirukawa |
| 5,065,929 A | 11/1991 | Schulze et al. |
| 5,071,430 A | 12/1991 | de Salis et al. |
| 5,129,570 A | 7/1992 | Schulze et al. |
| 5,137,198 A | 8/1992 | Nobis et al. |
| 5,139,513 A | 8/1992 | Segato |
| 5,158,567 A | 10/1992 | Green |
| 5,209,747 A | 5/1993 | Knoepfler |
| 5,211,649 A | 5/1993 | Kohler et al. |
| 5,221,036 A | 6/1993 | Takase |
| 5,222,975 A | 6/1993 | Crainich |
| 5,258,009 A | 11/1993 | Conners |
| 5,271,543 A | 12/1993 | Grant et al. |
| 5,282,806 A | 2/1994 | Haber et al. |
| 5,282,829 A | 2/1994 | Hermes |
| 5,304,204 A | 4/1994 | Bregen |
| 5,312,024 A | 5/1994 | Grant et al. |
| 5,318,221 A | 6/1994 | Green et al. |
| 5,342,395 A | 8/1994 | Jarrett et al. |
| 5,342,396 A | 8/1994 | Cook |
| 5,350,400 A | 9/1994 | Esposito et al. |
| 5,366,479 A | 11/1994 | McGarry et al. |
| 5,383,888 A | 1/1995 | Zvenyatsky et al. |
| 5,397,324 A | 3/1995 | Carroll et al. |
| 5,413,268 A | 5/1995 | Green et al. |
| 5,417,203 A | 5/1995 | Tovey et al. |
| 5,417,361 A | 5/1995 | Williamson, IV |
| 5,425,745 A | 6/1995 | Green et al. |
| 5,431,654 A | 7/1995 | Nic |
| 5,437,681 A | 8/1995 | Meade et al. |
| 5,456,401 A | 10/1995 | Green et al. |
| 5,465,894 A | 11/1995 | Clark et al. |
| 5,474,566 A | 12/1995 | Alesi et al. |
| 5,478,354 A | 12/1995 | Tovey et al. |
| 5,480,089 A | 1/1996 | Blewett |
| 5,482,197 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,509,596 A | 4/1996 | Green et al. |
| 5,514,157 A | 5/1996 | Nicholas et al. |
| 5,529,235 A | 6/1996 | Boiarski et al. |
| 5,535,934 A | 7/1996 | Boiarski et al. |
| 5,535,935 A | 7/1996 | Vidal et al. |
| 5,540,375 A | 7/1996 | Bolanos et al. |
| 5,542,594 A | 8/1996 | McKean et al. |
| 5,547,117 A | 8/1996 | Hamblin et al. |
| 5,553,765 A | 9/1996 | Knodel et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,575,799 A | 11/1996 | Bolanos et al. |
| 5,577,654 A | 11/1996 | Bishop |
| 5,580,067 A | 12/1996 | Hamblin et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,609,285 A | 3/1997 | Grant et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,645,209 A | 7/1997 | Green et al. |
| 5,647,526 A | 7/1997 | Green et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,527 A | 9/1997 | Cook |
| 5,669,544 A | 9/1997 | Schulze et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,685,474 A | 11/1997 | Seeber |
| 5,690,269 A | 11/1997 | Bolanos et al. |
| 5,692,668 A | 12/1997 | Schulze et al. |
| 5,697,543 A | 12/1997 | Burdorff |
| 5,702,408 A | 12/1997 | Wales et al. |
| 5,704,534 A | 1/1998 | Huitema et al. |
| 5,706,997 A | 1/1998 | Green et al. |
| 5,711,472 A | 1/1998 | Bryan |
| 5,713,505 A | 2/1998 | Huitema |
| 5,715,987 A | 2/1998 | Kelley et al. |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,743,456 A | 4/1998 | Jones et al. |
| 5,752,644 A | 5/1998 | Bolanos et al. |

| | | |
|---|---|---|
| 5,758,814 A | 6/1998 | Gallagher et al. |
| 5,762,255 A | 6/1998 | Chrisman et al. |
| 5,762,256 A | 6/1998 | Mastri et al. |
| 5,779,130 A | 7/1998 | Alesi et al. |
| 5,779,132 A | 7/1998 | Knodel et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,820,009 A | 10/1998 | Melling et al. |
| 5,826,776 A | 10/1998 | Schulze et al. |
| 5,833,695 A | 11/1998 | Yoon |
| 5,836,503 A | 11/1998 | Ehrenfels et al. |
| 5,839,639 A | 11/1998 | Sauer et al. |
| 5,855,311 A | 1/1999 | Hamblin et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,878,937 A | 3/1999 | Green et al. |
| 5,894,979 A | 4/1999 | Powell |
| 5,897,562 A | 4/1999 | Bolanos et al. |
| 5,901,895 A | 5/1999 | Heaton et al. |
| 5,904,693 A | 5/1999 | Dicesare et al. |
| 5,908,427 A | 6/1999 | McKean et al. |
| 5,911,353 A | 6/1999 | Bolanos et al. |
| 5,915,616 A | 6/1999 | Viola et al. |
| 5,919,198 A | 7/1999 | Graves, Jr. et al. |
| 5,941,442 A | 8/1999 | Geiste et al. |
| 5,954,259 A | 9/1999 | Viola et al. |
| 6,010,054 A | 1/2000 | Johnson et al. |
| 6,032,849 A | 3/2000 | Mastri et al. |
| 6,045,560 A | 4/2000 | McKean et al. |
| 6,047,861 A | 4/2000 | Vidal et al. |
| 6,050,472 A | 4/2000 | Shibata |
| 6,062,360 A | 5/2000 | Shields |
| 6,079,606 A | 6/2000 | Milliman et al. |
| 6,083,242 A | 7/2000 | Cook |
| 6,086,600 A | 7/2000 | Kortenbach |
| 6,099,551 A | 8/2000 | Gabbay |
| 6,102,271 A | 8/2000 | Longo et al. |
| 6,109,500 A | 8/2000 | Alli et al. |
| 6,119,913 A | 9/2000 | Adams et al. |
| 6,126,058 A | 10/2000 | Adams et al. |
| 6,155,473 A | 12/2000 | Tompkins et al. |
| 6,171,330 B1 | 1/2001 | Benchetrit |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,273,897 B1 | 8/2001 | Dalessandro et al. |
| 6,302,311 B1 | 10/2001 | Adams et al. |
| 6,315,184 B1 | 11/2001 | Whitman |
| 6,330,965 B1 | 12/2001 | Milliman et al. |
| 6,387,113 B1 | 5/2002 | Hawkins et al. |
| RE37,814 E | 8/2002 | Allgeyer |
| 6,436,107 B1 | 8/2002 | Wang et al. |
| 6,439,439 B1 | 8/2002 | Rickard et al. |
| 6,443,973 B1 | 9/2002 | Whitman |
| 6,488,197 B1 | 12/2002 | Whitman |
| 6,491,201 B1 | 12/2002 | Whitman |
| 6,505,768 B2 | 1/2003 | Whitman |
| 6,517,565 B1 | 2/2003 | Whitman et al. |
| 6,569,171 B2 | 5/2003 | DeGuillebon et al. |
| 6,578,751 B2 | 6/2003 | Hartwick |
| 6,588,643 B2 | 7/2003 | Bolduc et al. |
| 6,601,749 B2 | 8/2003 | Sullivan et al. |
| 6,616,686 B2 | 9/2003 | Coleman et al. |
| 6,619,529 B2 | 9/2003 | Green et al. |
| 6,629,988 B2 | 10/2003 | Weadock |
| 6,644,532 B2 | 11/2003 | Green et al. |
| 6,669,073 B2 | 12/2003 | Milliman et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,716,233 B1 | 4/2004 | Whitman |
| 6,755,338 B2 | 6/2004 | Hahnen et al. |
| 6,773,438 B1 | 8/2004 | Knodel et al. |
| 6,786,382 B1 | 9/2004 | Hoffman |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,830,174 B2 | 12/2004 | Hillstead et al. |
| 6,843,403 B2 | 1/2005 | Whitman |
| RE38,708 E | 3/2005 | Bolanos et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,960,107 B1 | 11/2005 | Schaub et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,008,435 B2 | 3/2006 | Cummins |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,056,330 B2 | 6/2006 | Gayton |
| 7,059,508 B2 | 6/2006 | Shelton, IV et al. |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,090,684 B2 | 8/2006 | McGuckin, Jr. et al. |
| 7,097,089 B2 | 8/2006 | Marczyk |
| 7,108,709 B2 | 9/2006 | Cummins |
| 7,111,769 B2 | 9/2006 | Wales et al. |
| 7,114,642 B2 | 10/2006 | Whitman |
| 7,118,582 B1 | 10/2006 | Wang et al. |
| 7,121,446 B2 | 10/2006 | Arad et al. |
| 7,128,253 B2 | 10/2006 | Mastri et al. |
| 7,140,527 B2 | 11/2006 | Ehrenfels et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,210,609 B2 | 5/2007 | Leiboff et |
| 7,213,736 B2 | 5/2007 | Wales et al. |
| 7,220,272 B2 | 5/2007 | Weadock |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,563 B1 | 10/2007 | Green |
| 7,296,724 B2 | 11/2007 | Green et al. |
| 7,297,149 B2 | 11/2007 | Vitali et al. |
| 7,303,106 B2 | 12/2007 | Milliman et al. |

| | | | | | | |
|---|---|---|---|---|---|---|
| 7,303,107 B2 | 12/2007 | Milliman et al. | | 2006/0047307 A1 | 3/2006 | Ortiz et al. |
| 7,303,108 B2 | 12/2007 | Shelton, IV | | 2006/0047308 A1* | 3/2006 | Ortiz et al. .................. 606/219 |
| 7,328,828 B2 | 2/2008 | Ortiz et al. | | 2006/0049229 A1 | 3/2006 | Milliman et al. |
| 7,328,829 B2 | 2/2008 | Arad et al. | | 2006/0052825 A1 | 3/2006 | Ransick et al. |
| 7,343,920 B2 | 3/2008 | Toby et al. | | 2006/0060630 A1 | 3/2006 | Shelton, IV et al. |
| 7,354,447 B2 | 4/2008 | Shelton, IV et al. | | 2006/0085033 A1 | 4/2006 | Criscuolo et al. |
| 7,380,695 B2 | 6/2008 | Doll et al. | | 2006/0100643 A1 | 5/2006 | Laufer et al. |
| 7,380,696 B2 | 6/2008 | Shelton, IV et al. | | 2006/0108393 A1 | 5/2006 | Heinrich et al. |
| 7,396,356 B2 | 7/2008 | Mollenauer | | 2006/0151567 A1 | 7/2006 | Roy |
| 7,398,907 B2 | 7/2008 | Racenet et al. | | 2006/0180634 A1 | 8/2006 | Shelton, IV et al. |
| 7,398,908 B2 | 7/2008 | Holsten et al. | | 2006/0190029 A1 | 8/2006 | Wales |
| 7,404,508 B2 | 7/2008 | Smith et al. | | 2006/0190031 A1 | 8/2006 | Wales et al. |
| 7,404,509 B2 | 7/2008 | Ortiz et al. | | 2006/0226196 A1 | 10/2006 | Hueil et al. |
| 7,407,075 B2 | 8/2008 | Holsten et al. | | 2006/0229665 A1 | 10/2006 | Wales et al. |
| 7,407,078 B2 | 8/2008 | Shelton, IV et al. | | 2006/0241692 A1 | 10/2006 | McGuckin, Jr. et al. |
| 7,410,086 B2 | 8/2008 | Ortiz et al. | | 2006/0273135 A1 | 12/2006 | Beetel |
| 7,416,101 B2 | 8/2008 | Shelton, IV et al. | | 2006/0278680 A1 | 12/2006 | Viola et al. |
| 7,422,136 B1 | 9/2008 | Marczyk | | 2006/0278681 A1 | 12/2006 | Viola et al. |
| 7,422,139 B2 | 9/2008 | Shelton, IV et al. | | 2006/0289602 A1 | 12/2006 | Wales et al. |
| 7,424,965 B2 | 9/2008 | Racenet et al. | | 2007/0023476 A1 | 2/2007 | Whitman et al. |
| 7,431,188 B1 | 10/2008 | Marczyk | | 2007/0023477 A1 | 2/2007 | Whitman et al. |
| 7,431,189 B2 | 10/2008 | Shelton, IV et al. | | 2007/0027469 A1 | 2/2007 | Smith et al. |
| 7,431,730 B2 | 10/2008 | Viola | | 2007/0034668 A1 | 2/2007 | Holsten et al. |
| 7,434,715 B2 | 10/2008 | Shelton, IV et al. | | 2007/0045379 A1 | 3/2007 | Shelton, IV |
| 7,434,717 B2 | 10/2008 | Shelton, IV et al. | | 2007/0084897 A1 | 4/2007 | Shelton, IV et al. |
| 7,438,209 B1 | 10/2008 | Hess et al. | | 2007/0102452 A1 | 5/2007 | Shelton, IV et al. |
| 7,441,684 B2 | 10/2008 | Shelton, IV et al. | | 2007/0102453 A1 | 5/2007 | Morgan et al. |
| 7,441,685 B1 | 10/2008 | Boudreaux | | 2007/0102472 A1 | 5/2007 | Shelton, IV |
| 7,448,525 B2 | 11/2008 | Shelton, IV et al. | | 2007/0102473 A1 | 5/2007 | Shelton, IV et al. |
| 7,464,846 B2 | 12/2008 | Shelton, IV et al. | | 2007/0102474 A1 | 5/2007 | Shelton, IV et al. |
| 7,464,847 B2 | 12/2008 | Viola et al. | | 2007/0106317 A1 | 5/2007 | Shelton, IV et al. |
| 7,464,849 B2 | 12/2008 | Shelton, IV et al. | | 2007/0114261 A1 | 5/2007 | Ortiz et al. |
| 7,467,740 B2 | 12/2008 | Shelton, IV et al. | | 2007/0158385 A1 | 7/2007 | Hueil et al. |
| 7,472,815 B2 | 1/2009 | Shelton, IV et al. | | 2007/0170225 A1 | 7/2007 | Shelton, IV et al. |
| 7,481,824 B2 | 1/2009 | Boudreaux et al. | | 2007/0175949 A1 | 8/2007 | Shelton, IV et al. |
| 7,490,749 B2 | 2/2009 | Schall et al. | | 2007/0175950 A1 | 8/2007 | Shelton, IV et al. |
| 7,494,039 B2 | 2/2009 | Racenet et al. | | 2007/0175951 A1 | 8/2007 | Shelton, IV et al. |
| 7,500,979 B2 | 3/2009 | Hueil et al. | | 2007/0175953 A1 | 8/2007 | Shelton, IV et al. |
| 7,506,790 B2 | 3/2009 | Shelton, IV | | 2007/0175955 A1 | 8/2007 | Shelton, IV et al. |
| 7,506,791 B2 | 3/2009 | Omaits et al. | | 2007/0175956 A1 | 8/2007 | Swayze et al. |
| 7,510,107 B2 | 3/2009 | Timm et al. | | 2007/0175957 A1 | 8/2007 | Shelton, IV et al. |
| 7,546,940 B2 | 6/2009 | Milliman et al. | | 2007/0175958 A1 | 8/2007 | Shelton, IV et al. |
| 7,549,564 B2 | 6/2009 | Boudreaux | | 2007/0175964 A1 | 8/2007 | Shelton, IV et al. |
| 7,568,603 B2 | 8/2009 | Shelton, IV et al. | | 2007/0179476 A1 | 8/2007 | Shelton, IV et al. |
| 7,631,793 B2 | 12/2009 | Rethy et al. | | 2007/0181632 A1 | 8/2007 | Milliman |
| 7,665,646 B2 | 2/2010 | Prommersberger | | 2007/0194079 A1 | 8/2007 | Hueil et al. |
| 2001/0027694 A1* | 10/2001 | Watarai .................... 74/502.2 | | 2007/0194080 A1 | 8/2007 | Swayze et al. |
| 2002/0117534 A1 | 8/2002 | Green et al. | | 2007/0194081 A1 | 8/2007 | Hueil et al. |
| 2004/0006372 A1 | 1/2004 | Racenet et al. | | 2007/0194082 A1 | 8/2007 | Morgan et al. |
| 2004/0034369 A1 | 2/2004 | Sauer et al. | | 2007/0233053 A1 | 10/2007 | Shelton, IV et al. |
| 2004/0094597 A1 | 5/2004 | Whitman et al. | | 2007/0246505 A1 | 10/2007 | Pace-Floridia et al. |
| 2004/0108357 A1 | 6/2004 | Milliman et al. | | 2007/0288044 A1 | 12/2007 | Jinno et al. |
| 2004/0164123 A1 | 8/2004 | Racenet et al. | | 2007/0295780 A1 | 12/2007 | Shelton et al. |
| 2004/0167572 A1 | 8/2004 | Roth et al. | | 2008/0029570 A1 | 2/2008 | Shelton et al. |
| 2004/0173659 A1 | 9/2004 | Green et al. | | 2008/0029573 A1 | 2/2008 | Shelton et al. |
| 2004/0222268 A1 | 11/2004 | Bilotti et al. | | 2008/0029574 A1 | 2/2008 | Shelton et al. |
| 2004/0232201 A1 | 11/2004 | Wenchell et al. | | 2008/0029575 A1 | 2/2008 | Shelton et al. |
| 2004/0243151 A1 | 12/2004 | Demmy et al. | | 2008/0029576 A1 | 2/2008 | Shelton et al. |
| 2004/0243176 A1 | 12/2004 | Hahnen et al. | | 2008/0035701 A1 | 2/2008 | Racenet et al. |
| 2004/0254608 A1 | 12/2004 | Huitema et al. | | 2008/0041917 A1 | 2/2008 | Racenet et al. |
| 2005/0059997 A1 | 3/2005 | Bauman et al. | | 2008/0078800 A1 | 4/2008 | Hess et al. |
| 2005/0070958 A1 | 3/2005 | Swayze et al. | | 2008/0078801 A1 | 4/2008 | Shelton et al. |
| 2005/0103819 A1 | 5/2005 | Racenet et al. | | 2008/0078802 A1 | 4/2008 | Hess et al. |
| 2005/0119669 A1 | 6/2005 | Demmy | | 2008/0078803 A1 | 4/2008 | Shelton et al. |
| 2005/0125009 A1 | 6/2005 | Perry et al. | | 2008/0078804 A1 | 4/2008 | Shelton et al. |
| 2005/0143759 A1 | 6/2005 | Kelly | | 2008/0078806 A1 | 4/2008 | Omaits et al. |
| 2005/0184121 A1 | 8/2005 | Heinrich | | 2008/0078807 A1 | 4/2008 | Hess et al. |
| 2005/0187576 A1 | 8/2005 | Whitman et al. | | 2008/0078808 A1 | 4/2008 | Hess et al. |
| 2005/0189397 A1 | 9/2005 | Jankowski | | 2008/0082115 A1 | 4/2008 | Morgan et al. |
| 2005/0216055 A1 | 9/2005 | Scirica et al. | | 2008/0082124 A1 | 4/2008 | Hess et al. |
| 2005/0263563 A1 | 12/2005 | Racenet et al. | | 2008/0082125 A1 | 4/2008 | Murray et al. |
| 2005/0274768 A1 | 12/2005 | Cummins et al. | | 2008/0082126 A1 | 4/2008 | Murray et al. |
| 2006/0011699 A1 | 1/2006 | Olson et al. | | 2008/0083813 A1 | 4/2008 | Zemlok et al. |

| | | | | | | |
|---|---|---|---|---|---|---|
| 2008/0140115 A1 | 6/2008 | Stopek | | 2009/0206144 A1 | 8/2009 | Doll et al. |
| 2008/0164296 A1 | 7/2008 | Shelton et al. | | 2009/0209946 A1 | 8/2009 | Swayze et al. |
| 2008/0167522 A1 | 7/2008 | Giordano et al. | | 2009/0218384 A1 | 9/2009 | Aranyi |
| 2008/0167644 A1 | 7/2008 | Shelton et al. | | 2009/0255974 A1 | 10/2009 | Viola |
| 2008/0167670 A1 | 7/2008 | Shelton et al. | | 2009/0255975 A1 | 10/2009 | Zemlok et al. |
| 2008/0167671 A1 | 7/2008 | Giordano et al. | | 2009/0255976 A1 | 10/2009 | Marczyk et al. |
| 2008/0167672 A1 | 7/2008 | Giordano et al. | | 2009/0255977 A1 | 10/2009 | Zemlok |
| 2008/0167736 A1 | 7/2008 | Swayze et al. | | 2009/0255978 A1 | 10/2009 | Viola et al. |
| 2008/0169328 A1 | 7/2008 | Shelton | | 2009/0289096 A1 | 11/2009 | Shelton, IV et al. |
| 2008/0169329 A1 | 7/2008 | Shelton et al. | | 2010/0032470 A1 | 2/2010 | Hess et al. |
| 2008/0169330 A1 | 7/2008 | Shelton et al. | | 2010/0065605 A1 | 3/2010 | Shelton, IV et al. |
| 2008/0169331 A1 | 7/2008 | Shelton et al. | | 2010/0065609 A1 | 3/2010 | Schwemberger |
| 2008/0169332 A1 | 7/2008 | Shelton et al. | | 2010/0069942 A1 | 3/2010 | Shelton, IV |
| 2008/0169333 A1 | 7/2008 | Shelton et al. | | 2010/0072251 A1 | 3/2010 | Baxter, III et al. |
| 2008/0183193 A1 | 7/2008 | Omori et al. | | 2010/0072252 A1 | 3/2010 | Baxter, III et al. |
| 2008/0197167 A1 | 8/2008 | Viola et al. | | 2010/0072253 A1 | 3/2010 | Baxter, III et al. |
| 2008/0210738 A1 | 9/2008 | Shelton et al. | | 2010/0072256 A1 | 3/2010 | Baxter, III et al. |
| 2008/0237296 A1 | 10/2008 | Boudreaux et al. | | 2010/0076474 A1 | 3/2010 | Yates et al. |
| 2008/0251568 A1 | 10/2008 | Zemlok et al. | | 2010/0076475 A1 | 3/2010 | Yates et al. |
| 2008/0290134 A1 | 11/2008 | Bettuchi et al. | | 2010/0089970 A1 | 4/2010 | Smith et al. |
| 2008/0296343 A1 | 12/2008 | Schall et al. | | 2010/0089974 A1 | 4/2010 | Shelton, IV |
| 2008/0296345 A1 | 12/2008 | Shelton, IV et al. | | 2010/0096435 A1 | 4/2010 | Fuchs et al. |
| 2008/0296346 A1 | 12/2008 | Shelton, IV et al. | | | | |
| 2008/0296347 A1 | 12/2008 | Shelton, IV et al. | | FOREIGN PATENT DOCUMENTS | | |
| 2008/0300580 A1 | 12/2008 | Shelton, IV et al. | | | | |
| 2008/0300613 A1 | 12/2008 | Shelton, IV et al. | | CA | 2512960 A1 | 1/2006 |
| 2008/0308601 A1 | 12/2008 | Timm et al. | | CA | 2514274 A1 | 1/2006 |
| 2008/0308602 A1 | 12/2008 | Timm et al. | | DE | 273689 C | 5/1914 |
| 2008/0308603 A1 | 12/2008 | Shelton, IV et al. | | DE | 1775926 A | 1/1972 |
| 2008/0308606 A1 | 12/2008 | Timm et al. | | DE | 9412228 U | 9/1994 |
| 2008/0308607 A1 | 12/2008 | Timm et al. | | DE | 19924311 A1 | 11/2000 |
| 2008/0308608 A1 | 12/2008 | Prommersberger | | DE | 69328576 T2 | 1/2001 |
| 2008/0314954 A1 | 12/2008 | Boudreaux | | DE | 20112837 U1 | 10/2001 |
| 2008/0314955 A1 | 12/2008 | Boudreaux et al. | | DE | 20121753 U1 | 4/2003 |
| 2008/0314957 A1 | 12/2008 | Boudreaux | | DE | 10314072 A1 | 10/2004 |
| 2008/0314960 A1 | 12/2008 | Marczyk et al. | | EP | 0122046 A1 | 10/1984 |
| 2008/0314961 A1 | 12/2008 | Boudreaux et al. | | EP | 0070230 B1 | 10/1985 |
| 2008/0314962 A1 | 12/2008 | Boudreaux | | EP | 0033548 B1 | 5/1986 |
| 2009/0001121 A1 | 1/2009 | Hess et al. | | EP | 0276104 A2 | 7/1988 |
| 2009/0001122 A1 | 1/2009 | Prommersberger et al. | | EP | 0639349 A2 | 2/1994 |
| 2009/0001123 A1 | 1/2009 | Morgan et al. | | EP | 0324636 B1 | 3/1994 |
| 2009/0001124 A1 | 1/2009 | Hess et al. | | EP | 0593920 A1 | 4/1994 |
| 2009/0001125 A1 | 1/2009 | Hess et al. | | EP | 0600182 A2 | 6/1994 |
| 2009/0001126 A1 | 1/2009 | Hess et al. | | EP | 0630612 A1 | 12/1994 |
| 2009/0001128 A1 | 1/2009 | Weisenburgh, II et al. | | EP | 0634144 A1 | 1/1995 |
| 2009/0001130 A1 | 1/2009 | Hess et al. | | EP | 0646356 A2 | 4/1995 |
| 2009/0005807 A1 | 1/2009 | Hess et al. | | EP | 0646357 A1 | 4/1995 |
| 2009/0005808 A1 | 1/2009 | Hess et al. | | EP | 0653189 A2 | 5/1995 |
| 2009/0005809 A1 | 1/2009 | Hess et al. | | EP | 0669104 A1 | 8/1995 |
| 2009/0012556 A1 | 1/2009 | Boudreaux et al. | | EP | 0511470 B1 | 10/1995 |
| 2009/0076534 A1 | 3/2009 | Shelton, IV et al. | | EP | 0679367 A2 | 11/1995 |
| 2009/0090763 A1 | 4/2009 | Zemlok et al. | | EP | 0392547 B1 | 12/1995 |
| 2009/0200355 A1 | 8/2009 | Baxter, III et al. | | EP | 0685204 A1 | 12/1995 |
| 2009/0206123 A1 | 8/2009 | Doll et al. | | EP | 0699418 A1 | 3/1996 |
| 2009/0206124 A1 | 8/2009 | Hall et al. | | EP | 0702937 A1 | 3/1996 |
| 2009/0206125 A1 | 8/2009 | Huitema et al. | | EP | 0705571 A1 | 4/1996 |
| 2009/0206126 A1 | 8/2009 | Huitema et al. | | EP | 0484677 B2 | 6/1996 |
| 2009/0206128 A1 | 8/2009 | Hueil et al. | | EP | 0541987 B1 | 7/1996 |
| 2009/0206129 A1 | 8/2009 | Doll et al. | | EP | 0667119 B1 | 7/1996 |
| 2009/0206130 A1 | 8/2009 | Hall et al. | | EP | 0770355 A1 | 5/1997 |
| 2009/0206131 A1 | 8/2009 | Weisenburgh, II et al. | | EP | 0503662 B1 | 6/1997 |
| 2009/0206132 A1 | 8/2009 | Hueil et al. | | EP | 0578425 B1 | 9/1997 |
| 2009/0206133 A1 | 8/2009 | Morgan et al. | | EP | 0625335 B1 | 11/1997 |
| 2009/0206134 A1 | 8/2009 | Swayze et al. | | EP | 0552423 B1 | 1/1998 |
| 2009/0206135 A1 | 8/2009 | Hall et al. | | EP | 0592244 B1 | 1/1998 |
| 2009/0206136 A1 | 8/2009 | Moore et al. | | EP | 0648476 B1 | 1/1998 |
| 2009/0206137 A1 | 8/2009 | Hall et al. | | EP | 0676173 B1 | 9/1998 |
| 2009/0206138 A1 | 8/2009 | Smith et al. | | EP | 0603472 B1 | 11/1998 |
| 2009/0206139 A1 | 8/2009 | Hall et al. | | EP | 0605351 B1 | 11/1998 |
| 2009/0206140 A1 | 8/2009 | Scheib et al. | | EP | 0878169 A1 | 11/1998 |
| 2009/0206141 A1 | 8/2009 | Huitema et al. | | EP | 0879742 A1 | 11/1998 |
| 2009/0206142 A1 | 8/2009 | Huitema et al. | | EP | 0760230 B1 | 2/1999 |
| 2009/0206143 A1 | 8/2009 | Huitema et al. | | EP | 0537572 B1 | 6/1999 |

| | | | | | | |
|---|---|---|---|---|---|---|
| EP | 0552050 B1 | 5/2000 | | JP | 2000287987 A | 10/2000 |
| EP | 1090592 A1 | 4/2001 | | JP | 2001286477 A | 10/2001 |
| EP | 1256318 B1 | 5/2001 | | JP | 2002369820 A | 12/2002 |
| EP | 0908152 B1 | 1/2002 | | JP | 2005505322 T | 2/2005 |
| EP | 0872213 B1 | 5/2002 | | JP | 2005103293 A | 4/2005 |
| EP | 1238634 A2 | 9/2002 | | RU | 2187249 C2 | 8/2002 |
| EP | 0656188 B1 | 1/2003 | | RU | 2225170 C2 | 3/2004 |
| EP | 0829235 B1 | 6/2003 | | SU | 1377053 A1 | 2/1988 |
| EP | 0813843 B1 | 10/2003 | | SU | 1561964 A1 | 5/1990 |
| EP | 0741996 B1 | 2/2004 | | SU | 1722476 A1 | 3/1992 |
| EP | 0705570 B1 | 4/2004 | | WO | WO 93/08755 A1 | 5/1993 |
| EP | 1086713 B1 | 5/2004 | | WO | WO 95/18572 A1 | 7/1995 |
| EP | 1426012 A1 | 6/2004 | | WO | WO 95/23557 A1 | 9/1995 |
| EP | 0888749 B1 | 9/2004 | | WO | WO 95/29639 A1 | 11/1995 |
| EP | 1477119 A1 | 11/2004 | | WO | WO 96/22055 A1 | 7/1996 |
| EP | 1479345 A1 | 11/2004 | | WO | WO 96/35464 A1 | 11/1996 |
| EP | 1479347 A1 | 11/2004 | | WO | WO 97/34533 A1 | 9/1997 |
| EP | 1479348 A1 | 11/2004 | | WO | WO 97/39688 A2 | 10/1997 |
| EP | 1520521 A1 | 4/2005 | | WO | WO 98/17180 A1 | 4/1998 |
| EP | 1520523 A1 | 4/2005 | | WO | WO 98/30153 A1 | 7/1998 |
| EP | 1520525 A1 | 4/2005 | | WO | WO 99/12483 A1 | 3/1999 |
| EP | 1522264 A1 | 4/2005 | | WO | WO 99/15086 A1 | 4/1999 |
| EP | 1550408 A1 | 7/2005 | | WO | WO 99/34744 A1 | 7/1999 |
| EP | 1557129 A1 | 7/2005 | | WO | WO 99/45849 A1 | 9/1999 |
| EP | 1064883 B1 | 8/2005 | | WO | WO 00/24322 A1 | 5/2000 |
| EP | 1157666 B1 | 9/2005 | | WO | WO 00/57796 A1 | 10/2000 |
| EP | 1621138 A2 | 2/2006 | | WO | WO 00/64365 A1 | 11/2000 |
| EP | 1621139 A2 | 2/2006 | | WO | WO 00/72762 A1 | 12/2000 |
| EP | 1621141 A2 | 2/2006 | | WO | WO 00/72765 A1 | 12/2000 |
| EP | 1621145 A2 | 2/2006 | | WO | WO 01/05702 A1 | 1/2001 |
| EP | 1652481 A2 | 5/2006 | | WO | WO 01/10482 A1 | 2/2001 |
| EP | 1382303 B1 | 6/2006 | | WO | WO 01/54594 A1 | 8/2001 |
| EP | 1045672 B1 | 8/2006 | | WO | WO 01/62158 A2 | 8/2001 |
| EP | 1617768 B1 | 8/2006 | | WO | WO 01/62162 A1 | 8/2001 |
| EP | 1702567 A2 | 9/2006 | | WO | WO 01/62164 A2 | 8/2001 |
| EP | 1129665 B1 | 11/2006 | | WO | WO 01/91646 A1 | 12/2001 |
| EP | 1256317 B1 | 12/2006 | | WO | WO 02/07608 A2 | 1/2002 |
| EP | 1728473 A1 | 12/2006 | | WO | WO 02/07618 A1 | 1/2002 |
| EP | 1728475 A2 | 12/2006 | | WO | WO 02/17799 A1 | 3/2002 |
| EP | 1479346 B1 | 1/2007 | | WO | WO 02/19920 A1 | 3/2002 |
| EP | 1484024 B1 | 1/2007 | | WO | WO 02/30297 A2 | 4/2002 |
| EP | 1754445 A2 | 2/2007 | | WO | WO 02/32322 A2 | 4/2002 |
| EP | 1759812 A1 | 3/2007 | | WO | WO 02/43571 A2 | 6/2002 |
| EP | 1769756 A1 | 4/2007 | | WO | WO 02/058568 A1 | 8/2002 |
| EP | 1769758 A1 | 4/2007 | | WO | WO 02/60328 A1 | 8/2002 |
| EP | 1785097 A2 | 5/2007 | | WO | WO 02/67785 A2 | 9/2002 |
| EP | 1790293 A2 | 5/2007 | | WO | WO 02/098302 A1 | 12/2002 |
| EP | 1300117 B1 | 8/2007 | | WO | WO 03/000138 A2 | 1/2003 |
| EP | 1813199 A1 | 8/2007 | | WO | WO 03/001329 A2 | 1/2003 |
| EP | 1813201 A1 | 8/2007 | | WO | WO 03/013363 A1 | 2/2003 |
| EP | 1813203 A2 | 8/2007 | | WO | WO 03/020106 A2 | 3/2003 |
| EP | 1813207 A1 | 8/2007 | | WO | WO 03/020139 A2 | 3/2003 |
| EP | 1813209 A1 | 8/2007 | | WO | WO 03/079909 A3 | 3/2003 |
| EP | 1839596 A1 | 10/2007 | | WO | WO 03/030743 A2 | 4/2003 |
| EP | 1872727 A1 | 1/2008 | | WO | WO 03/037193 A1 | 5/2003 |
| EP | 1897502 A1 | 3/2008 | | WO | WO 03/047436 A3 | 6/2003 |
| EP | 1702568 B1 | 7/2008 | | WO | WO 03/057048 A1 | 7/2003 |
| EP | 1980213 A2 | 10/2008 | | WO | WO 03/057058 A1 | 7/2003 |
| EP | 1759645 B1 | 11/2008 | | WO | WO 03/063694 A1 | 8/2003 |
| EP | 1693008 B1 | 12/2008 | | WO | WO 03/077769 A1 | 9/2003 |
| EP | 1749486 B1 | 3/2009 | | WO | WO 03/082126 A1 | 10/2003 |
| EP | 2090256 A2 | 8/2009 | | WO | WO 03/088845 A2 | 10/2003 |
| EP | 1813206 B1 | 4/2010 | | WO | WO 03/090630 A2 | 11/2003 |
| FR | 999646 A | 2/1952 | | WO | WO 03/094743 A1 | 11/2003 |
| FR | 1112936 A | 3/1956 | | WO | WO 03/094745 A1 | 11/2003 |
| FR | 2765794 A | 1/1999 | | WO | WO 03/094746 A1 | 11/2003 |
| GB | 939929 A | 10/1963 | | WO | WO 03/094747 A1 | 11/2003 |
| GB | 1210522 A | 10/1970 | | WO | WO 03/101313 A1 | 12/2003 |
| GB | 2336214 A | 10/1999 | | WO | WO 03/105698 A2 | 12/2003 |
| JP | 6007357 A | 1/1994 | | WO | WO 03/105702 A2 | 12/2003 |
| JP | 7051273 A | 2/1995 | | WO | WO 2004/006980 A2 | 1/2004 |
| JP | 8033641 A | 2/1996 | | WO | WO 2004/028585 A2 | 4/2004 |
| JP | 8229050 A | 9/1996 | | WO | WO 2004/032754 A2 | 4/2004 |

| | | | |
|---|---|---|---|
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/078892 A1 | 8/2005 |
| WO | WO 2005/096954 A2 | 10/2005 |
| WO | WO 2005/112808 A1 | 12/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/115958 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |

OTHER PUBLICATIONS

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

European Search Report, Application No. 09250390.3, dated Jul. 28, 2009 (9 pages).

Partial European Search Report, Application 08251908.3, dated Jan. 5, 2010 (11 pages).

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

\* cited by examiner

SURGICAL STAPLING AND CUTTING INSTRUMENT WITH ARTICULATABLE END EFFECTOR

FIELD OF THE INVENTION

The present invention relates in general to endoscopic surgical instruments including, but not limited to, surgical stapler instruments that are capable of applying lines of staples to tissue while cutting the tissue between those staple lines and, more particularly, to improvements relating to articulation joints used in connection with surgical stapler instruments with articulatable end effectors.

BACKGROUND

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument commonly includes a plurality of reciprocating wedges which, when driven distally, pass through openings in the staple cartridge and engage drivers supporting the staples to effect the firing of the staples toward the anvil.

Examples of surgical staplers suitable for endoscopic applications are described in U.S. Pat. No. 6,905,057 to Jeffrey S. Swayze and Frederick E. Shelton, IV, entitled Surgical Stapling Instrument Incorporating a Firing Mechanism Having a Linked Rack Transmission and U.S. Pat. No. 7,083,075 to Jeffery S. Swayze, Frederick E. Shelton, IV, Kevin Ross Doll, and Douglas B. Hoffman entitled Multi-Stroke Mechanism With Automatic End of Stroke Retractions, the disclosures of which are herein incorporated by reference in their entireties.

Depending upon the nature of the operation, it may be desirable to further adjust the positioning of the end effector of an endoscopic surgical instrument. In particular, it is often desirable to orient the end effector at an angle relative to the longitudinal axis of the shaft of the instrument. The transverse or non-axial movement of the end effector relative to the instrument shaft is often conventionally referred to as "articulation". This articulated positioning permits the clinician to more easily engage tissue in some instances, such as behind an organ. In addition, articulated positioning advantageously allows an endoscope to be positioned behind the end effector without being blocked by the instrument shaft.

Approaches to articulating a surgical stapling and severing instrument tend to be complicated by integrating control of the articulation along with the control of closing the end effector to clamp tissue and fire the end effector (i.e., stapling and severing) within the small diameter constraints of an endoscopic instrument. Generally, the three control motions are all transferred through the shaft as longitudinal translations. For instance, U.S. Pat. No. 5,673,840 to Schulze et al., the disclosure of which is herein incorporated by reference, discloses an accordion-like articulation mechanism ("flexneck") that is articulated by selectively drawing back one of two connecting rods through the implement shaft, each rod offset respectively on opposite sides of the shaft centerline. The connecting rods ratchet through a series of discrete positions.

Another example of longitudinal control of an articulation mechanism is U.S. Pat. No. 5,865,361 that includes an articulation link offset from a camming pivot such that pushing or pulling longitudinal translation of the articulation link effects articulation to a respective side. Similarly, U.S. Pat. No. 5,797,537 discloses a similar rod passing through the shaft to effect articulation. Still other examples of articulatable surgical stapling devices are disclosed in U.S. Pat. Nos. 6,250,532 and 6,644,532.

Due to the types end effector firing systems commonly employed, the actuator arrangements for articulating the end effector must often generate high amounts of torque to bend the firing structure. This problem is exacerbated by the lack of available space for accommodating actuating devices that are large enough to generated those required forces.

In an effort to address such challenges, surgical instruments with "passive articulation joints" have been developed. For example, U.S. Patent Publication No. US 2007/0027469 A1 to Kevin W. Smith, Matthew A. Palmer, Korey Robert Kline and Derek Dee Deville, the disclosure of which is herein incorporated by reference, discloses a medical device that employs a passive articulation joint. When actuated, the articulation joint is released into a freely articulating state to permit free articulation of the end effector with respect to the control handle dependent upon external forces acting upon the end effector.

While the above-mentioned medical device with a passive articulation arrangement effectively addresses various challenges encountered with active articulation arrangements, there is still a need for medical devices with improved passive articulation joint arrangements.

SUMMARY

In one aspect of the invention, there is provided a surgical instrument that may include a handle portion and a proximal frame portion that is coupled to the handle portion and has a plurality of first planetary gear teeth formed thereon. The instrument may further comprise an end effector for performing a surgical operation. The end effector may have a plurality of second planetary gear teeth formed thereon. At least one pivot bar is pivotally coupled to the proximal frame portion and distal frame portion to retain the first gear teeth in permanent meshing orientation with the second gear teeth to facilitate pivotal travel of the end effector relative to the proximal frame portion.

In another general aspect of various embodiments of the present invention there is provided a surgical instrument that may include a handle portion and a proximal frame portion that is coupled to the handle portion. The instrument may further include an end effector for performing a surgical operation. At least two flexible bands are attached to the proximal frame portion and the end effector and extend therebetween such that at least one of the at least two flexible bands crosses another one of the at least two flexible bands.

In still another general aspect of various embodiments of the present invention there is provided a surgical instrument that may include a handle portion and a proximal frame portion that is coupled to the handle portion. The instrument may further include an end effector for performing a surgical operation. A series of interlocking flexible sockets are coupled to the proximal frame portion and the end effector and extend therebetween.

In another general aspect of various embodiments of the present invention there is provided a surgical instrument that may include a handle portion and a proximal frame portion that is coupled to the handle portion. The proximal frame portion may define a longitudinal axis. The instrument may further include an end effector for performing a surgical operation. At least two substantially rigid bars may be pivotally attached to the proximal frame portion and the end effector and extend therebetween such that one end of at least one of the rigid bars is attached to the proximal frame portion along the longitudinal axis.

In another general aspect of various embodiments of the present invention there is provided a surgical instrument that may include a handle portion and a proximal frame portion that is coupled to the handle portion. The proximal frame portion may define a longitudinal axis. The instrument may further include an end effector for performing a surgical operation that is coupled to the proximal frame portion by an articulation joint. The articulation joint may include first and second arcuate slots in one of the end effector and the proximal frame portion. Each arcuate slot is oriented to slidably receive therein a corresponding pin that protrudes from the other of the end effector and proximal frame portion to facilitate pivotal travel of the end effector relative to the proximal frame portion about a pivot axis that is substantially transverse to the longitudinal axis.

In another general aspect of various embodiments of the present invention there is provided a surgical instrument that may include a handle portion and a proximal frame portion that is coupled to the handle portion. The proximal frame portion may define a longitudinal axis. The instrument may further include an end effector for performing a surgical operation that is coupled to the proximal frame portion by an articulation joint. The articulation joint may include a concave surface defining a bowl on one of the proximal frame portion and the end effector. A convex surface may be formed on the other of the proximal frame portion and the end effector and be in confronting relationship with the concave surface to define a pivot axis extending through the convex and concave surfaces about which the end effector may pivot relative to the proximal frame portion such that the end effector can only pivot in one plane that is substantially perpendicular to the pivot axis.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain various principles of the present invention.

DETAILED DESCRIPTION

Figure 1:
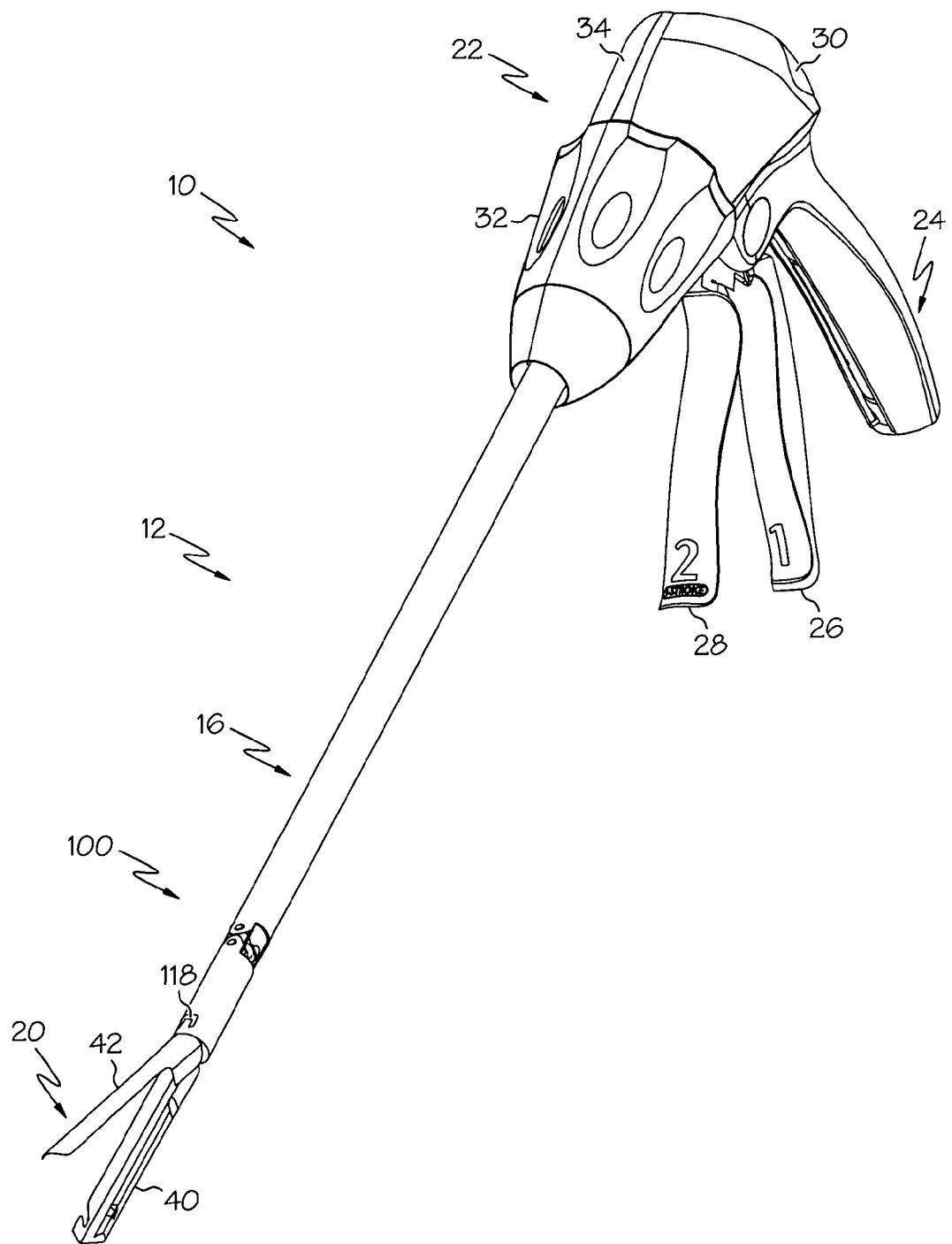
FIG. 1 is a perspective view of a surgical stapling and severing instrument of various embodiments of the present invention.

Turning to the Drawings, wherein like numerals denote like components throughout the several views, FIG. 1 depicts a surgical instrument, which in the illustrative versions is more particularly a surgical stapling and severing instrument 10, capable of practicing the unique benefits of the present invention. In particular, the surgical stapling and severing instrument 10 is sized for insertion, in a nonarticulated state as depicted in FIG. 1, through a trocar cannula passageway to a surgical site in a patient (not shown) for performing a surgical procedure. An end effector, depicted in the illustrative version as a staple applying assembly 20, is distally attached to a shaft portion 16 by an articulation joint 100. After the staple applying assembly 20 has been inserted through the trocar cannula passageway, the clinician can move the staple applying assembly 20 to a desired articulated orientation by "passively" bringing the staple applying assembly 20 into contact with the organ or other portion of the body or another medical instrument to apply an external force to the staple applying instrument 20 to cause it to articulate as will be discussed in further detail below. Such an angled position may have advantages in approaching tissue from a desired angle for severing and stapling, approaching tissue otherwise obstructed by other organs and tissue, and/or allowing an endoscope to be positioned behind and aligned with the staple applying assembly 20 for confirming placement.

The surgical and stapling and severing instrument 10 may include a handle portion 22 proximally connected to the implement portion 12 for providing positioning, articulation, closure and firing motions thereto. The handle portion 22 may include a pistol grip 24 toward which a closure trigger 26 is pivotally and proximally drawn by the clinician to cause clamping, or closing, of the staple applying assembly 20. A firing trigger 28 may be positioned further outboard of the closure trigger 26 and is capable of being pivotally drawn by the clinician to cause the stapling and severing of tissue clamped in the staple applying assembly 20. Thereafter, a closure release button 30 is depressed to release the clamped closure trigger 26, and thus the severed and stapled ends of the clamped tissue. The handle portion 22 also includes a rotation knob 32 coupled for movement with the elongate shaft 16 to rotate the shaft 16 and the articulated staple applying assembly 20 about the longitudinal axis of the shaft 16. The handle portion 22 also includes a firing retraction handle 34 to assist in retracting a firing mechanism (not depicted in FIG. 1) should binding occur, so that opening of the staple applying assembly 20 may occur thereafter.

It will be appreciated that the terms "proximal" and "distal" are used herein with reference to a clinician gripping a handle of an instrument. Thus, the surgical stapling assembly 20 is distal with respect to the more proximal handle portion 22. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

Figure 2:
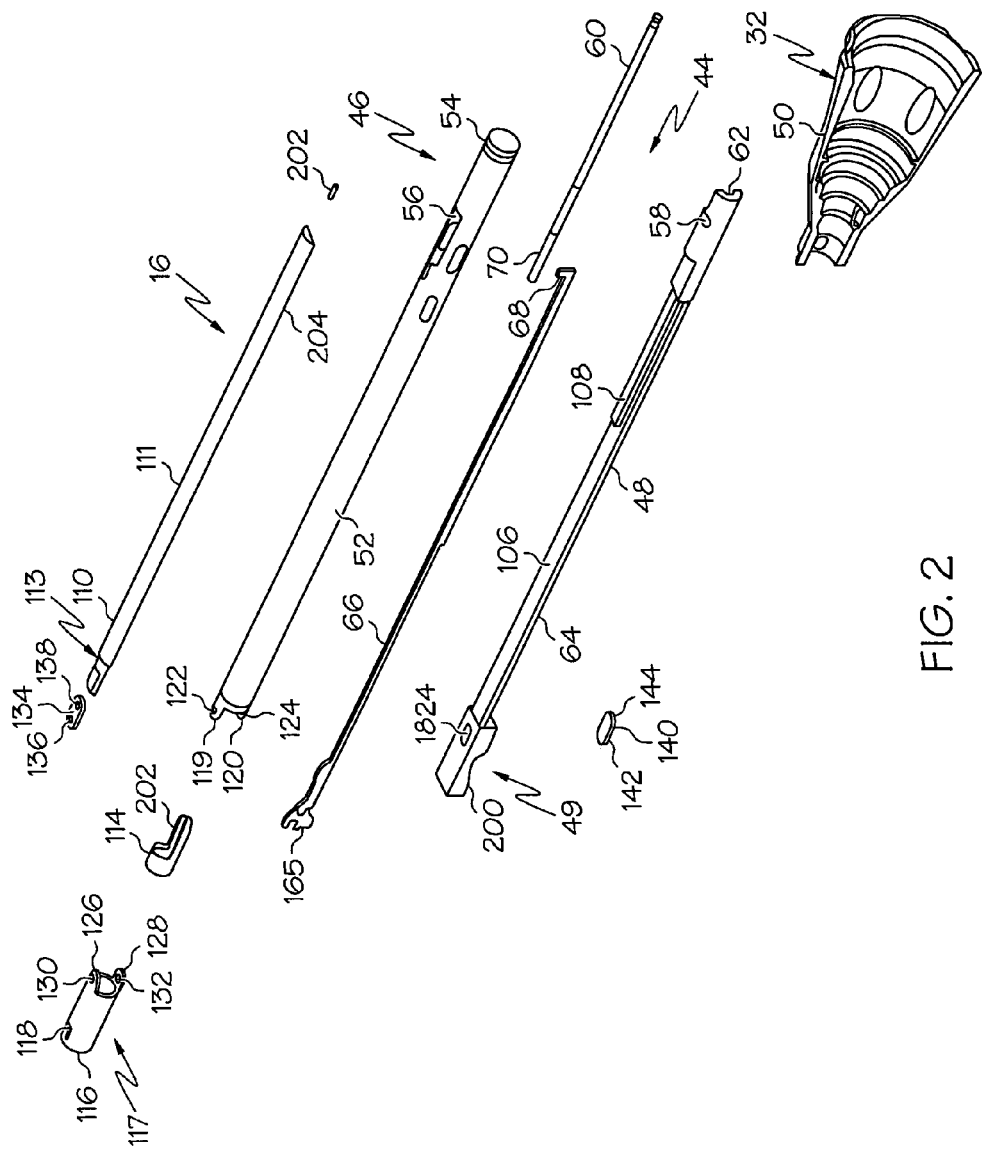
FIG. 2 is a perspective disassembled view of an elongate shaft and articulation mechanism of the surgical stapling and severing instrument of FIG. 1.

An illustrative multi-stroke handle portion 22 for the surgical stapling and severing instrument 10 of FIGS. 1-2 is described in greater detail in the following co-pending and commonly-owned U.S. patent applications, the disclosures of which are herein incorporated by reference, with additional features and variations as described herein:

(1) U.S. Patent Publication No. US 2006/0289602A1 to Kenneth S. Wales and Eugene L. Timperman, entitled "Surgical Instrument With Articulating Shaft With Double Pivot Closure And Single Pivot Frame Portion;

(2) U.S. Patent Publication No. US 2006/0190029A1 to Kenneth S. Wales, entitled "Surgical Instrument With Laterally Moved Shaft Actuator Coupled to Pivoting Articulation Joint;

(3) U.S. Patent Publication No. US 2006/0190031 A1 to Kenneth S. Wales and Cad P. Boudreaux, entitled "Surgical Instrument With Articulating Shaft With Rigid Firing Bar Supports"; and.

(4) U.S. Publication No. 20050070958 A1 to Swayze and Shelton IV, entitled "Surgical Stapling Instrument Incorporating a Multistroke Firing Position Indicator and Retraction Mechanism".

While a multi-stroke handle portion 22 advantageously supports applications with high firing forces over a long distance, applications consistent with the present invention may incorporate a single firing stroke, such as described in co-pending and commonly owned U.S. Pat. No. 7,000,818, entitled "Surgical Stapling Instrument Having Separate Distinct Closing and Firing Systems" to Frederick E. Shelton IV, Michael E. Setser, and Brian J. Hemmelgarn, the disclosure of which is hereby incorporated by reference in its entirety.

Figure 3:
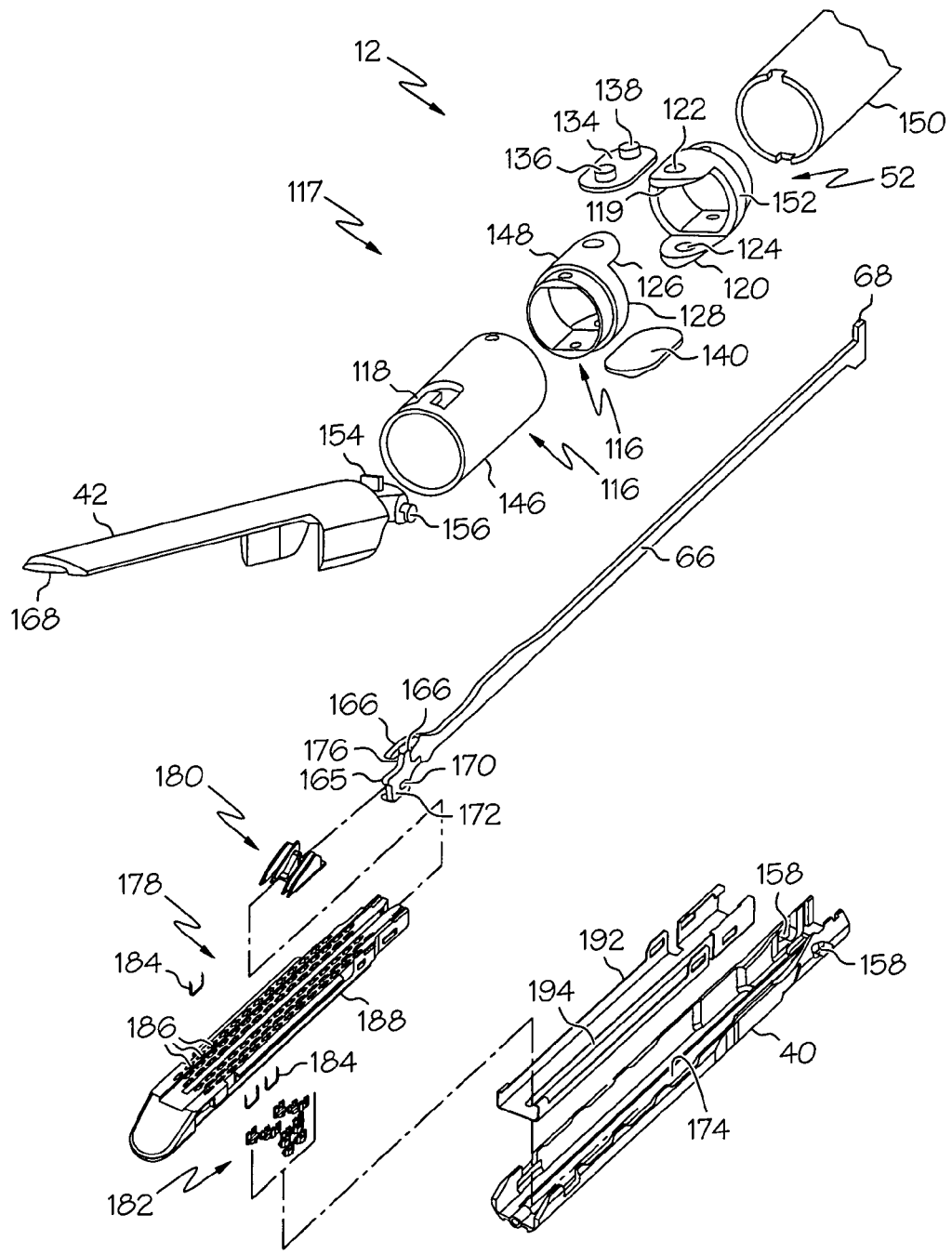
FIG. 3 is a perspective disassembled view of distal portions of an implement portion of the surgical stapling and severing instrument of FIG. 1.

In FIGS. 2 and 3, the implement portion 12 may advantageously incorporate the multiple actuation motions of longitudinal rotation, articulation, closure and firing within a small diameter suitable for endoscopic and laparoscopic procedures. The staple applying assembly 20 ("end effector") has a pair of pivotally opposed jaws, depicted as an elongate channel 40 with a pivotally attached anvil 42 (FIGS. 1 and 3). Closure and clamping of the anvil 42 to the elongate channel 40 is achieved by longitudinally supporting the elongate channel 40 with a frame assembly 44 (FIG. 2) rotatingly attached to the handle portion 22 over which a double pivot closure sleeve assembly 46 longitudinally moves to impart closing and opening motions respectively to the anvil 42, even with the staple applying assembly 20 articulated.

With particular reference to FIG. 2, the frame assembly 44 may include a single pivot frame portion 48 whose proximal end is engaged to the rotation knob 32, with a right half shell 50 thereon shown in FIG. 2. It should be appreciated that a proximal end of the closure sleeve assembly 46, specifically of closure straight tube 52, encompasses the proximal end of the frame portion 48, passing further internally to the handle portion 22 to engage closure components (not shown) that longitudinally translate the closure sleeve assembly 46. A circular lip 54 at the proximal end of the closure straight tube 52 provides a rotating engagement to such components. Engaging components of the rotation knob 32 pass through a longitudinal slot 56 on a proximal portion of the straight closure tube 52 to engage an aperture 58 proximally positioned on the frame portion 48. The longitudinal slot 56 is of sufficient length to allow the closure longitudinal translation of the closure sleeve assembly 46 at various rotational angles set by the rotation knob 32 to the closure sleeve assembly 46 and the frame portion 48.

The elongate shaft 16 supports the firing motion by receiving a firing rod 60 that rotatingly engages firing components of the handle portion 22 (not shown). The firing rod 60 enters a proximal opening 62 along the longitudinal centerline of the frame portion 48. The distal portion of the frame portion 48 includes a firing bar slot 64 along its bottom that communicates with the proximal opening 62. A firing bar 66 longitudinally translates in the firing bar slot 64 and includes an upwardly projecting proximal pin 68 that engages a distal end 70 of the firing rod 60.

With particular reference to FIG. 3, the articulation joint 100 may include a distal closure tube segment 116 that may be constructed as shown for enhanced manufacturability and may include a short closure tube 146 that is attached to an articulating attachment collar 148 that may include proximally projecting pivot tabs 126, 128. Similarly, the straight closure tube 52 may be assembled from a long closure tube segment 150 that attaches to an aft attachment collar 152 that may include the distally projecting pivot tabs 119, 120. The horseshoe aperture 118 in the short tube 146 is designed to engages an upwardly projecting anvil feature 154 that is slightly proximal to lateral pivot pins 156 that engage pivot recesses 158 inside of the elongate channel 40. See FIG. 3.

In various embodiments, the firing bar 66 may distally terminate in an E-beam 165 that includes upper guide pins 166 that enter an anvil slot 168 in the anvil 42 to verify and assist in maintaining the anvil 42 in a closed state during staple formation and severing. See FIG. 3. Spacing between the elongate channel 40 and anvil 42 may be further maintained by the E-beam 165 by having middle pins 170 slide along the top surface of the elongate channel 40 while a bottom foot 172 opposingly slides along the undersurface of the elongate channel 40, guided by a longitudinal opening 174 in the elongate channel 40. A distally presented cutting surface 176 of the E-beam 165, which is between the upper guide pins 166 and middle pin 170, severs clamped tissue while the E-beam actuates a replaceable staple cartridge 178 by distally moving a wedge sled 180 that causes staple drivers 182 to cam upwardly driving staples 184 out of upwardly open staple holes 186 in a staple cartridge body 188, forming against a staple forming undersurface 190 of the anvil 42. A staple cartridge tray 192 encompasses from the bottom the other components of the staple cartridge 178 to hold them in place. The staple cartridge tray 192 includes a rearwardly open slot 194 that overlies the longitudinal opening 174 in the elongate channel 40, thus the middle pins 170 pass inside of the staple cartridge tray 192. One form of a and end effector or staple applying assembly that may be employed is described in greater detail in co-pending and commonly-owned U.S. Patent Publication No. 20070084897 A1, entitled "Articulating Surgical Stapling Instrument Incorporating a Two-Piece E-Beam Firing Mechanism" to Frederick E. Shelton IV, et al., the disclosure of which is hereby incorporated by reference in its entirety.

Figure 4:
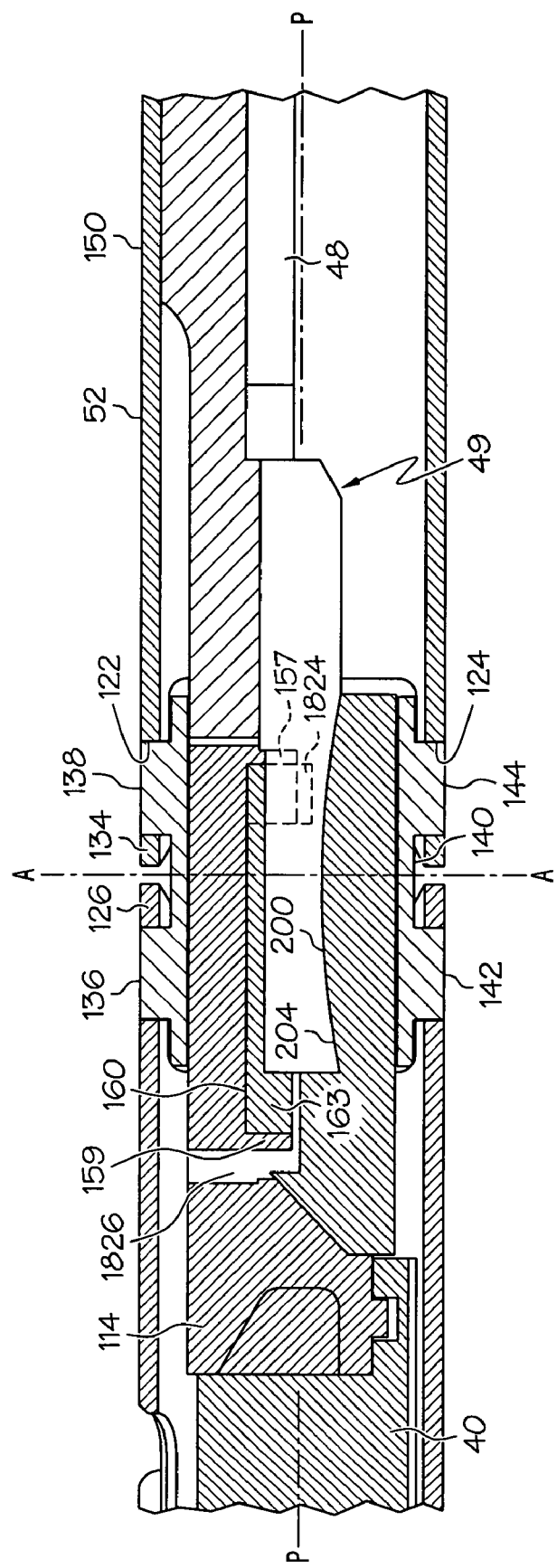
FIG. 4 is a cross-sectional elevational view of an articulation joint of one embodiment of the present invention.

With reference to FIGS. 2-4, the articulation joint 100 may advantageously incorporate the double pivot closure sleeve assembly 46 described above. One exemplary arrangement of these mechanisms and their operation will now be described in further detail. In various embodiments, for example, the distal end 49 of the proximal frame portion 48 may be provided with a downwardly facing concave lower surface 200 that is adapted to receive a correspondingly shaped convex surface 204 on the distal frame member 114. Those of ordinary skill in the art will appreciate that, in an alternative embodiment, the concave surface may be provided on the distal frame member 114 and the convex surface may be formed on the proximal frame portion 48 without departing from the spirit and scope of the present invention.

Such joint arrangement 100 facilitates pivotal travel of the distal frame member 114 relative to the proximal frame portion 48 around a pivot axis, generally referenced as axis A-A in FIG. 4 such that the distal frame member 114 (and staple applying assembly 20) is generally pivotable about axis A-A in a plane "P-P" in which the proximal frame portion 48 also lies. As shown in FIG. 4, axis A-A is substantially perpendicular to a plane P-P. Stated another way, such arrangement of concave and convex surfaces 200, 204 restricts rotation of the distal frame member 114 about pivot axis A-A relative to the proximal frame portion 48 within a common plane of rotation P-P. Thus, this joint arrangement does not enable the distal frame member 114 to pivot in a plane that is substantially different from a plane in which the proximal frame portion 48 lies. Such arrangement does, however, afford relatively easy pivoting and rotation of the staple applying assembly 20. When the closure sleeve assembly 46 is moved distally to pivot anvil 42 closed, the closure tube 52 moves distally about proximal frame portion 48 and the articulated distal closure tube segment 116 moves distally along the articulated distal frame member 114 as urged by pivot links 134, 140. Dual pivoting pins 136, 138 and 142, 144 on links 134, 140, respectively, facilitate engagement with closure tube 52 and articulated distal closure tube segment 116 as they are urged towards the distal closure position when the device is articulated (not shown).

Figure 5:
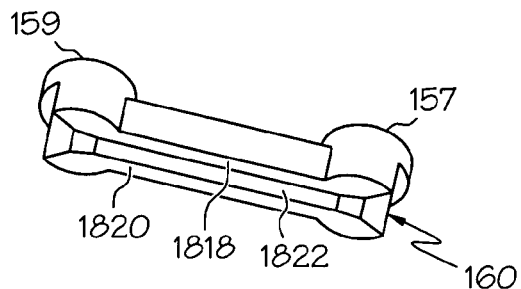
FIG. 5 is a perspective view of a dog bone link that may be employed with various embodiments of the present invention.

In various embodiments, a dog bone link 160 may be employed and configured to provide support to the firing bar 66 which may be of flexible construction. The frame portion 48 may also include a frame knife slot (not shown) that runs along the bottom of frame portion 48 and a distal knife slot (not shown) that runs along the bottom of the distal frame member 114 for the sliding reception of the firing bar 66 (not shown) therein. The dog bone link 160 may be rotatably connected on proximal pin end 157 and movably connected on distal pin end 159 and include left and right lateral guides 1818, 1820, defining therebetween a guidance slot 1822 for sliding passage of a firing bar 66 (FIG. 5). Thus, to bridge the gap between frame portion 48 and the distal frame member 114, the fixed wall pivoting dog bone link 160 is pivotally attached to frame portion 48 and slidingly attached to distal frame member 114. Proximal pin 157 of the pivoting dog bone 160 is pivotally received in a bore 1824 in frame portion 48 enabling pivotal dog bone 160 to pivot therein. A distal pin 159 extends from pivotal dog bone 160 and is slidingly received in a slot 1826 in distal frame member 114. Articulation of staple applying assembly 20 to an angle of such as 45 degrees from the longitudinal axis pivots pivoting dog bone 160 in bore 1824 at its proximal pin 157, and distal pin 157 slides in slot 1826 at its distal end 1814 to bend firing bar 66 to two spaced apart angles that are half of the angle of the staple applying assembly 20.

The distal frame member 114 can pivot relative to the proximal frame portion 48 about pivot axis A-A by virtue of the concave and convex surface arrangement. Those of ordinary skill in the art will understand that in various embodiments the friction between the surfaces 200 and 204 will serve to retain the distal frame member 114 (and the staple applying assembly 20) in the articulated position relative to the proximal frame portion 48 and additional clamping arrangements may be used to apply clamping forces thereto to retain those components in the desired articulated position. The end effector may be articulated by applying an articulation force thereto by bringing the end effector into contact with a portion of the patient's body or with another instrument which may also be inserted into the patient's body.

Figure 6:
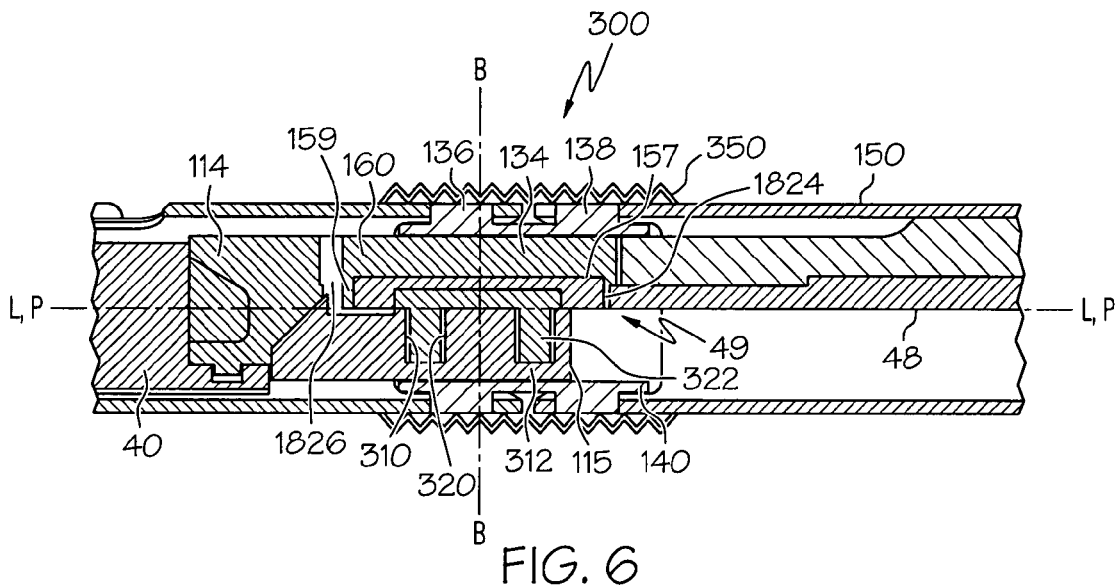
FIG. 6 is a cross-sectional elevational view of an articulation joint of another embodiment of the present invention.
Figure 7:
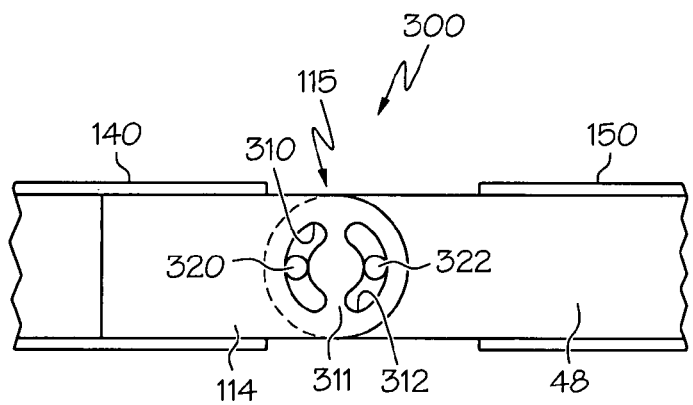
FIG. 7 is a top view of the articulation joint of FIG. 6 illustrating the position of certain components in diagrammatical form.

FIGS. 6 and 7 illustrate another articulation joint 300 that may be employed in connection with various embodiments of the present invention. This embodiment may be substantially identical in construction to the above-described embodiment, except for the following differences. For example, in this embodiment, the proximal end 115 of the distal frame member 114 may have two arcuate slots 310, 312 formed therein for receiving corresponding pins 320, 322 formed on the distal end 49 of the proximal frame portion 48. Thus, the distal frame member 114 is constrained to pivot relative to the frame portion 48 by the travel of the pins 320, 322 in their respective slots 310, 312 about pivot axis B-B that extends through the center 311 between the arcuate slots 310, 312. Pivot axis B-B may be substantially perpendicular to the longitudinal axis L-L of the proximal frame portion 48. This joint arrangement may also serve to restrict the pivotal travel of the distal frame member 114 about the pivot axis B-B such that the distal frame member 114 is substantially retained in the common plane of rotation P-P with the proximal frame portion 48. Those of ordinary skill in the art will appreciate that in alternative embodiments, the arcuate slots 310, 312 may be provided in the distal end 49 of the proximal frame portion 48 and the pins 320, 322 may be provided in the distal frame member 114 without departing from the spirit and scope of the present invention. In still other embodiments, the distal frame member 114 and the proximal frame portion 48 may each have one arcuate slot and one pin wherein the pin is oriented to be slidably received in the slot in the other part.

Also in these embodiments, to bridge the gap between frame portion 48 and the distal frame member 114, the fixed wall pivoting dog bone link 160 may pivotally attached to frame portion 48 and slidingly attached to distal frame member 114. Proximal pin 157 of the pivoting dog bone 160 is pivotally received in a bore 1824 in frame portion 48 enabling pivotal dog bone 160 to pivot therein. A distal pin 159 extends from pivotal dog bone 160 and is slidingly received in a slot 1826 in distal frame 114. Articulation of staple applying assembly 20 to an angle of such as 45 degrees from the longitudinal axis pivots pivoting dog bone 160 in bore 1824 at its proximal pin 157, and distal pin 157 slides in slot 1826 at its distal end 1814 to bend firing bar 66 to two spaced apart angles that are half of the angle of the staple applying assembly 20. In various embodiments, a bellows-like sleeve or cover 350 made from an elastomeric or polymeric material may be positioned over the shaft to at the location of the articulation joint to prevent debris and fluids from entering the joint. See FIG. 6. The end effector may be articulated by applying an articulation force thereto by bringing the end effector into contact with a portion of the patient's body or with another instrument which may also be inserted into the patient's body.

Figure 8:
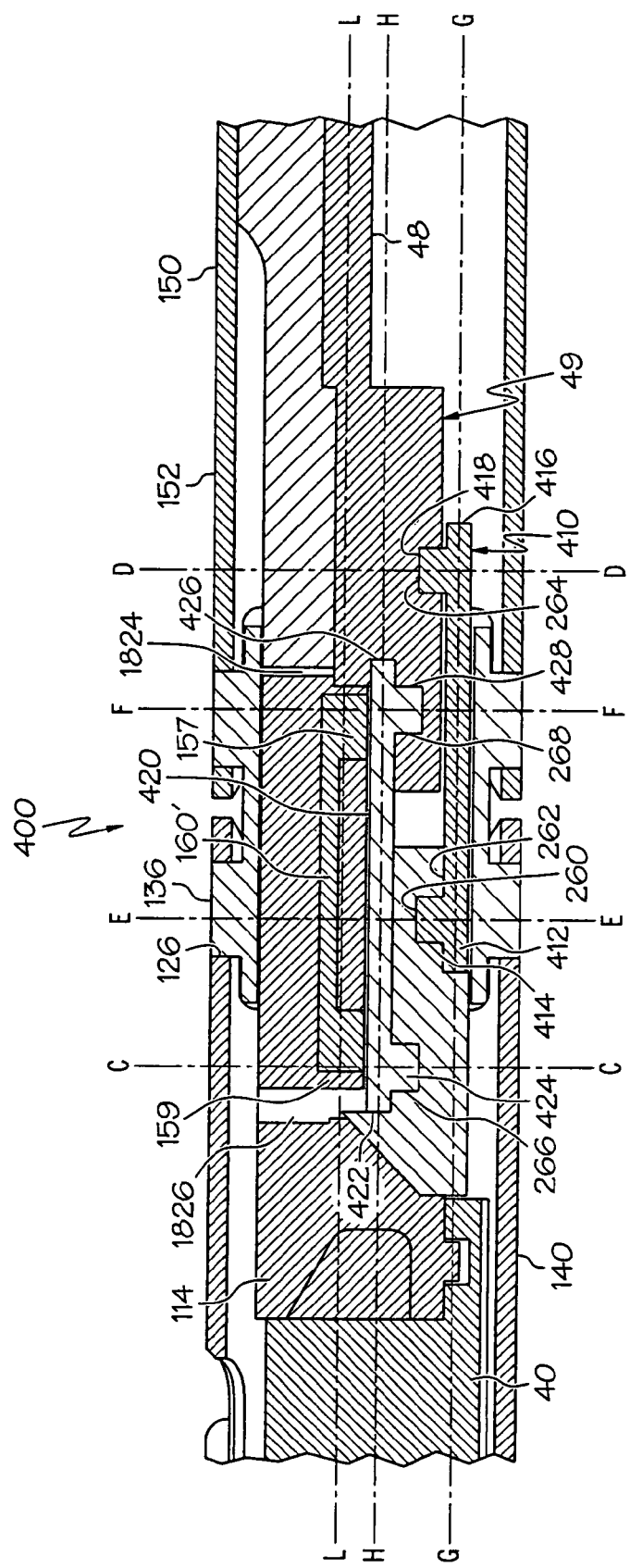
FIG. 8 is a cross-sectional elevational view of an articulation joint of another embodiment of the present invention.
Figure 9:
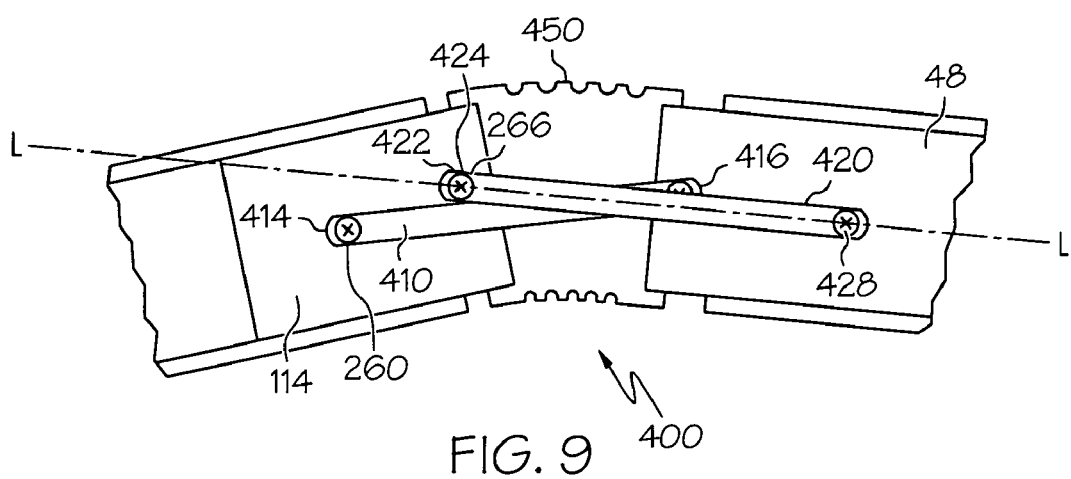
FIG. 9 is a top view of the articulation joint of FIG. 8 to illustrate the position of certain components in diagrammatical form.

FIGS. 8 and 9 illustrate another articulation joint 400 that may be employed in connection with various embodiments of the present invention. This embodiment may be substantially identical in construction to the above-described embodiments, except for the following differences. For example, this embodiment may employ a pair of substantially rigid linkage bars 410, 420 to pivotally interconnect the distal frame member 114 and the frame portion 48. As can be seen in FIG. 8, for example, the lower linkage bar 410 may have a distal pin portion 414 protruding from a distal end 412 thereof that is constructed to be received in a first hole 260 in the distal frame member 114. Distal frame member 114 may also be provided with an undercut portion 262 to accommodate the pivotal travel of the distal end 412 of the lower linkage bar 410 therein about a first pivot axis C-C defined by the distal pin 414 and hole 262. As can also be seen in FIG. 8, the proximal end 416 of the lower linkage bar 410 may have a proximal pin 418 protruding therefrom that is constructed to be received within a hole 264 in the distal end 49 of the frame portion 48. The proximal pin 418 and hole 264 also serve to define a second pivot axis D-D.

As indicated above, this embodiment may further comprise an upper linkage bar 420 that has a distal end 422 and a proximal end 426. A distal pin 424 protrudes from the distal end 422 and is constructed to be received in a second hole 266 in the distal frame member 114. The pin 424 and the hole 266 serve to define a third pivot axis E-E. A proximal pin 428 protrudes from the proximal end 426 of the upper linkage bar 420 and is constructed to be received in a second hole 268 in the distal end 49 of the frame portion 48. The proximal pin 428 and hole 268 serve to define a fourth pivot axis F-F. As can be seen in FIG. 8, the first axis C-C, the second axis D-D, the third axis E-E, and the fourth axis F-F may all be substantially transverse and perpendicular to the longitudinal axis L-L of the proximal frame portion 48. As can also be seen in FIG. 9, at least one of the pins 424, 428 lie along longitudinal axis L-L.

Also in this embodiment, to bridge the gap between frame portion 48 and the distal frame member 114, the fixed wall pivoting dog bone link 160 may pivotally attached to frame portion 48 and slidingly attached to frame member 114. Proximal pin 157 of the pivoting dog bone 160 is pivotally received in a bore 1824 in frame portion 48 enabling pivotal dog bone 160 to pivot therein. A distal pin 159 extends from pivotal dog bone 160 and is slidingly received in a slot 1826 in distal frame 114. As can be seen in FIG. 8, the lower linkage bar 410 lies along a lower plane G-G and the upper linkage bar 420 lies along an upper plane H-H that is not coplanar with the lower plane G-G. Such arrangement enables the linkage bars 410, 420 to pivot to an axially aligned position wherein the shaft 16 can be inserted through a trocar passage (FIG. 1) and other non-axially aligned articulated positions (FIG. 9). In various embodiments, a bellows-like sleeve 450 made from an elastomeric or polymeric material may be positioned over the shaft to at the location of the articulation joint 400 to prevent debris and fluids from entering the joint. See FIG. 9. The end effector may be articulated by applying an articulation force thereto by bringing the end effector into contact with a portion of the patient's body or with another instrument which may also be inserted into the patient's body.

Figure 10:
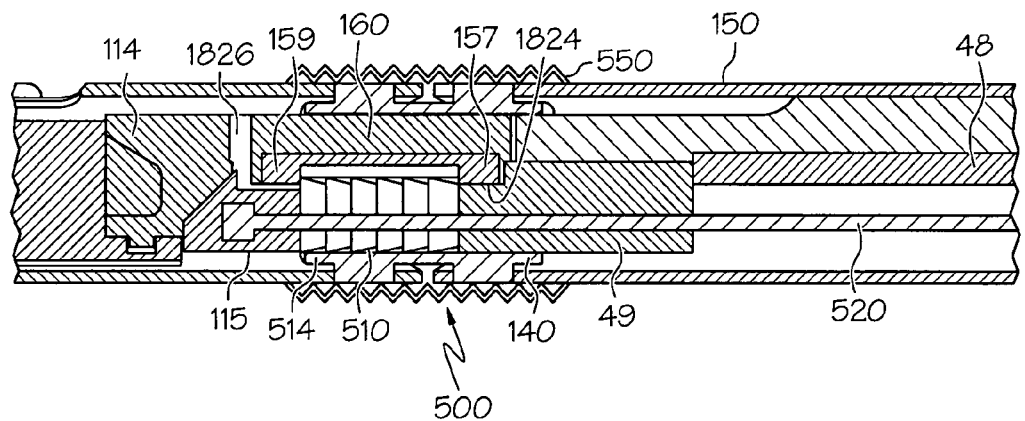
FIG. 10 is a cross-sectional elevational view of an articulation joint of another embodiment of the present invention.
Figure 11:
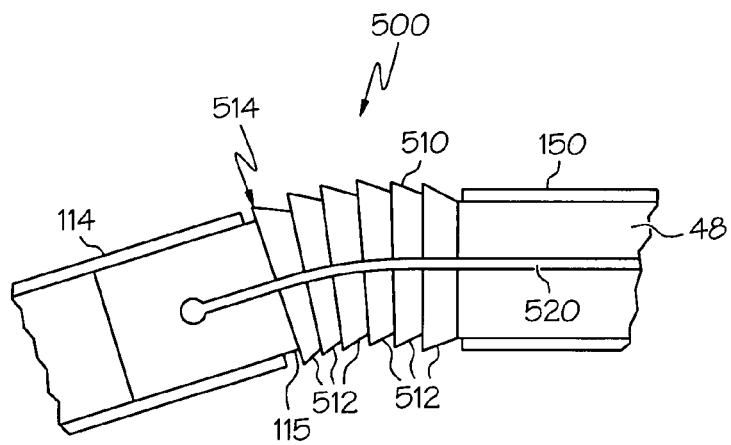
FIG. 11 is a top view of the articulation joint of FIG. 10 to illustrate the position of certain components in diagrammatical form.

FIGS. 10 and 11 illustrate another articulation joint 500 that may be employed in connection with various embodiments of the present invention. This embodiment may be substantially identical in construction to the above-described embodiments, except for the following differences. For example, this embodiment may employ a series 510 of flexible interlocking sockets 512 for pivotally and rotatably interconnecting the distal frame member 114 and the frame portion 48. As can be seen in FIG. 10, for example, a proximal end of the series of flexible interlocking sockets may be attached to the distal end 49 of the frame portion 48. A distal end 514 of the series 510 may be attached to the proximal end 115 of the frame member 114. A tension cable 520 may be employed such that it extends from the handle portion (not shown) through the proximal closure tube segment 150 and is coupled to the frame member 114. When tension is applied to the cable 520, the sockets 512 interlock to retain the sockets 512 in the substantially locked position. To reposition the staple applying assembly 20, tension is relaxed on the cable 520 to thereby permit the application of an external force to the staple applying assembly 20 to enable it to be articulated and/or rotated to a desired orientation. Once the staple applying assembly 20 has been positioned in the desired orientation, tension is reapplied to the cable 520 to retain the interlocking sockets 512 in position.

Also in this embodiment, to bridge the gap between frame portion 48 and the distal frame member 114, the fixed wall pivoting dog bone link 160 may pivotally attached to frame portion 48 and slidingly attached to frame member 114. Proximal pin 157 of the pivoting dog bone 160 is pivotally received in a bore 1824 in frame portion 48 enabling pivotal dog bone 160 to pivot therein. A distal pin 159 extends from pivotal dog bone 160 and is slidingly received in a slot 1826 in distal frame 114. In various embodiments, a bellows-like sleeve 550 made from an elastomeric or polymeric material may be positioned over the shaft to at the location of the articulation joint to prevent debris and fluids from entering the joint. See FIG. 10. The end effector may be articulated by applying an articulation force thereto by bringing the end effector into contact with a portion of the patient's body or with another instrument which may also be inserted into the patient's body.

Figure 12:
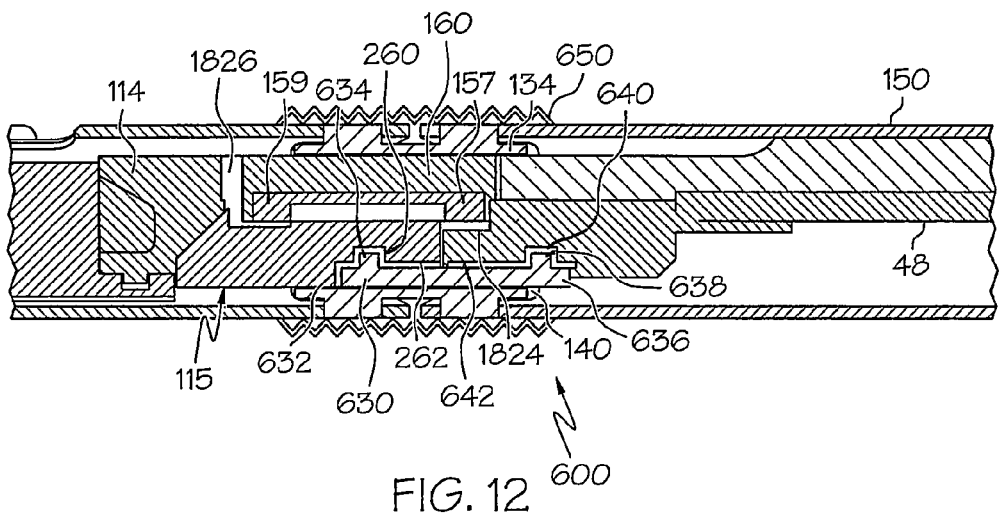
FIG. 12 is a cross-sectional elevational view of an articulation joint of another embodiment of the present invention.
Figure 13:
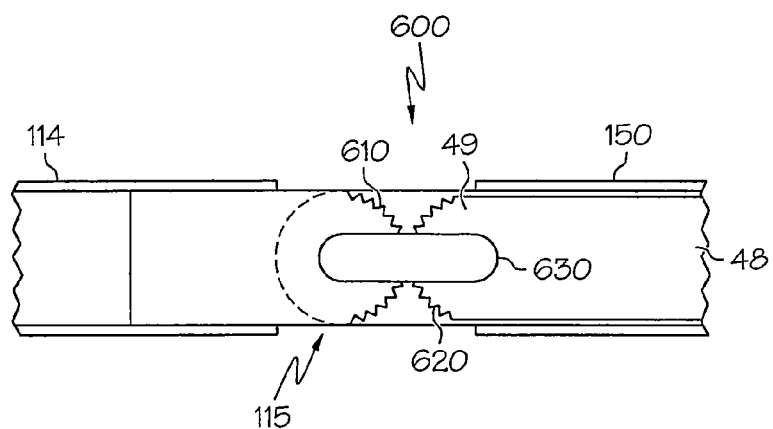
FIG. 13 is a top view of the articulation joint of FIG. 12 to illustrate the position of certain components in diagrammatical form.

FIGS. 12 and 13 illustrate another articulation joint 600 that may be employed in connection with various embodiments of the present invention. This embodiment may be substantially identical in construction to the above-described embodiments, except for the following differences. For example, in this embodiment, a first series of planetary-like gear teeth 610 may be formed on at least a portion of the circumference of the proximal end 115 of the frame member 114. Likewise a second series of planetary-like gear teeth 620 are formed on at least a portion of the circumference of the distal end 49 of the frame portion 48. The gear teeth 610 are retained in permanent meshing engagement with gear teeth 620 by a pivot bar 630 that pivotally interconnects the proximal end 115 of the frame member 114 with the distal end 49 of the frame portion 48. As can be seen in FIG. 12, a distal pin portion 634 protrudes from a distal end 632 of the pivot bar 630 and is constructed to be rotatably received in a hole 260 formed in the underside of the frame member 114. The frame member 114 may also have an undercut area 262 formed therein to accommodate the pivotal travel of the pivot bar 630. Likewise, a proximal end 636 of the pivot bar 630 has a proximal pin portion 638 that protrudes therefrom and is sized to be rotatably received in a hole 640 in the frame portion 48. An undercut area 642 may also be provided in the distal end 49 of the frame portion 48 to accommodate the pivotal travel of the pivot bar 630.

Also in this embodiment, to bridge the gap between frame portion 48 and the distal frame member 114, the fixed wall pivoting dog bone link 160 may pivotally attached to frame portion 48 and slidingly attached to frame member 114. Proximal pin 157 of the pivoting dog bone 160 is pivotally received in a bore 1824 in frame portion 48 enabling pivotal dog bone 160 to pivot therein. A distal pin 159 extends from pivotal dog bone 160 and is slidingly received in a slot 1826 in distal frame 114. In various embodiments, a bellows-like sleeve 650 made from an elastomeric or polymeric material may be positioned over the shaft to at the location of the articulation joint to prevent debris and fluids from entering the joint. See FIG. 12.

Figure 14:
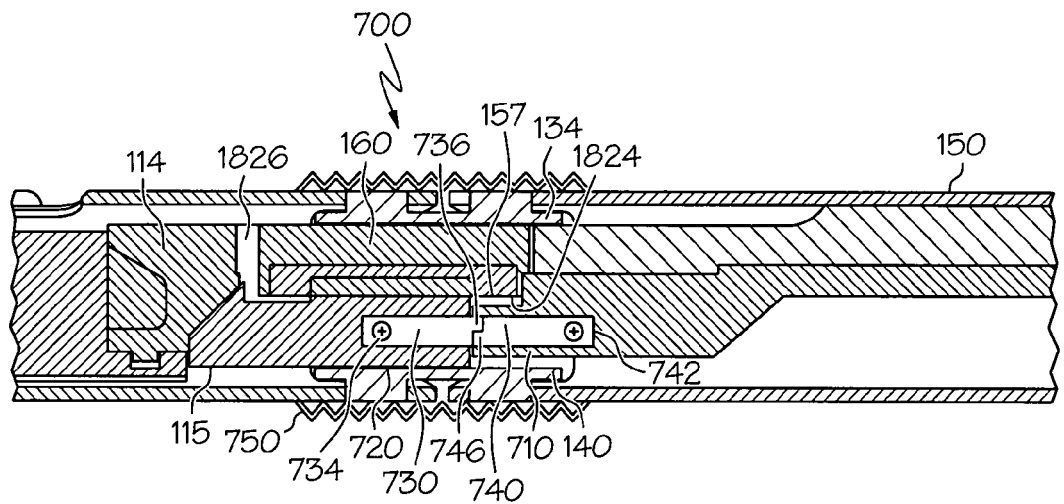
FIG. 14 is a cross-sectional elevational view of an articulation joint of another embodiment of the present invention.
Figure 15:
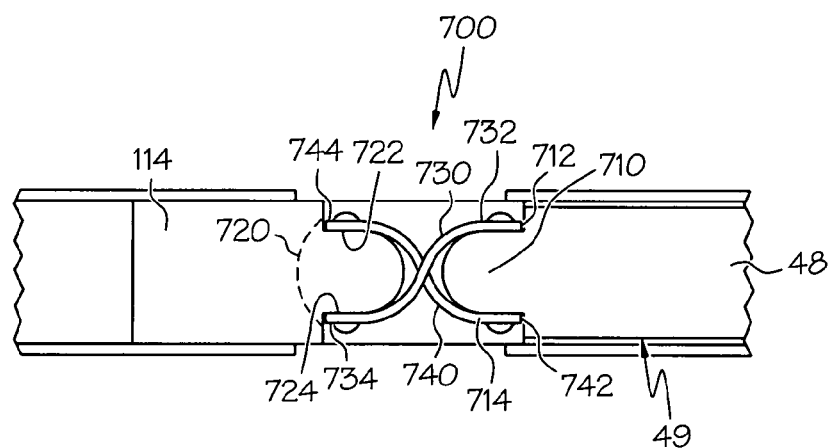
FIG. 15 is a top view of the articulation joint of FIG. 6 to illustrate the position of certain components in diagrammatical form.

FIGS. 14 and 15 illustrate another articulation joint 700 that may be employed in connection with various embodiments of the present invention. This embodiment may be substantially identical in construction to the above-described embodiments, except for the following differences. For example, in this embodiment, the distal end 49 of the frame portion 48 is formed as a protrusion 710 extending in a distal direction. In various embodiments, the distal protrusion 710 has a first lateral side 712 and a second lateral side 714. Similarly, the proximal end 115 of the distal frame member 114 is also formed as a protrusion 720 that extends in the proximal direction in confronting relationship relative to the distal protrusion 710. The proximal protrusion 720 has a primary lateral side 722 that corresponds to the first lateral side 712 of the distally extending protrusion 710. The proximally extending protrusion 720 further has a secondary lateral side 724 that corresponds to the second lateral side 714 of the distally extending protrusion 710.

In this embodiment, the flexible joint 700 may further include a first flexible band 730 that has a proximal end 732 attached to the first lateral side 712 of the distally extending protrusion 710 and a distal end 734 attached to the secondary lateral side 724 of the proximally extending protrusion 720. This embodiment may further include a second flexible band 740 that has a proximal end 742 attached to the second lateral side 714 of the distally extending protrusion 710 and a distal end 744 that is attached to the primary lateral side 722 of the proximally extending protrusion 720. In various embodiments the first flexible band 730 and second flexible band 740 may be fabricated from spring steel or other suitable flexible materials and be attached to the protrusions 710, 720, respectively, by suitable fastener arrangements such as screws, adhesive, etc. As can be seen in FIG. 14, the first flexible band has a first notch 736 therein and the second flexible band 740 has a second notch 746 therein to enable the bands 730, 740 to be arranged as shown in FIG. 15.

Also in this embodiment, to bridge the gap between frame portion 48 and the distal frame member 114, the fixed wall pivoting dog bone link 160 may pivotally attached to frame portion 48 and slidingly attached to frame member 114. Proximal pin 157 of the pivoting dog bone 160 is pivotally received in a bore 1824 in frame portion 48 enabling pivotal dog bone 160 to pivot therein. A distal pin 159 extends from pivotal dog bone 160 and is slidingly received in a slot 1826 in distal frame 114. In various embodiments, a bellows-like sleeve 750 made from an elastomeric or polymeric material may be positioned over the shaft to at the location of the articulation joint to prevent debris and fluids from entering the joint. See FIG. 14. The end effector may be articulated by applying an articulation force thereto by bringing the end effector into contact with a portion of the patient's body or with another instrument which may also be inserted into the patient's body.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The devices disclosed herein can be designed to be disposed of after a single use, or they can be designed to be used multiple times. In either case, however, the device may be reconditioned for reuse after at least one use. Reconditioning may include any combination of the steps of disassembly of the device, followed by cleaning or replacement of particular pieces, and subsequent reassembly. In particular, the device may be disassembled, and any number of particular pieces or parts of the device can be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A surgical instrument, comprising:
a handle portion;
a proximal frame portion coupled to said handle portion and defining a longitudinal axis;
an end effector for performing a surgical operation;
a lower rigid bar pivotally attached to said proximal frame portion and said end effector and extending therebetween, said lower rigid bar lying along a first plane; and
an upper rigid bar lying along a second plane that is not coplanar with said first plane and being pivotally attached to said proximal frame portion and said end effector and extending therebetween such that one end of at least one said upper and lower rigid bars is attached to said proximal frame portion along said longitudinal axis.

2. A surgical instrument, comprising:
a handle portion;
a proximal frame portion coupled to said handle portion and defining a longitudinal axis;
an end effector for performing a surgical operation;
an upper rigid bar having a distal end pivotally attached to said end effector for pivotal travel relative thereto about a first axis substantially transverse to said longitudinal axis and a proximal end pivotally attached to said proximal frame portion for pivotal travel relative thereto about a second axis that is substantially transverse to said longitudinal axis; and
a lower rigid bar having a distal end pivotally attached to said end effector for pivotal travel relative thereto about a third axis that is substantially transverse to said longitudinal axis and a proximal end pivotally attached to said proximal frame portion for pivotal travel relative thereto about a fourth axis that is substantially transverse to said longitudinal axis.

3. The surgical instrument of claim 2 wherein said proximal frame portion extends through a proximal closure tube segment operably coupled to said handle portion and wherein said surgical instrument further comprises a distal closure tube segment pivotally coupled to said proximal closure tube segment and constructed to apply closing and opening motions to said end effector.

4. The surgical instrument of claim 3 further comprising a flexible cover member extending between said proximal closure tube segment and said distal closure tube segment for preventing debris from entering therebetween.

* * * * *